US00PP09871P

United States Patent [19]

Sherman

[11] Patent Number: Plant 9,871

[45] Date of Patent: Apr. 29, 1997

[54] NECTARINE TREE CALLED "SUNMIST"

[76] Inventor: Wayne B. Sherman, 2230 SW. 43 Pl., Gainsville, Fla. 32608

[21] Appl. No.: 303,036

[22] Filed: Aug. 22, 1994

[51] Int. Cl.[6] ..... A01H 5/00

[52] U.S. Cl. ..... Plt./40.1

[58] Field of Search ..... Plt./40.1

[56] References Cited

PUBLICATIONS

Sherman, et al., "'Sunmist' Nectarine" *HortScience* 30(1): 155. 1995.

*Primary Examiner*—James R. Feyrer

[57] ABSTRACT

A new and distinct variety of nectarine tree, *Prunus persica*, which has a low winter chilling requirement of approximately 300 chill units (cu). The tree is of large size, is highly vigorous, has a spreading growth habit and has showy pink flowers. The flowers have terra cotta (red) anthers. Glands are reniform in shape and isolated on the basal portions of the leave. This tree, which has been denominated 'Sunmist' is a regular bearer of heavy crops of early maturing, large (for early ripening season), semi-freestone fruit with white flesh color. Fruit is uniform, attractive, substantially symmetrical shape, and has an attractive normally nearly solid ruby to red over-color. The fruit ripens substantially with that of 'Sunred', but is larger, firmer and of very good eating quality.

3 Drawing Sheets

BACKGROUND OF THE VARIETY

In a continuing effort to improve the quality of stone fruit to create a new variety available to growers and consumers, the breeder (inventor) typically makes sufficient crosses to produce one to three thousand seedlings each year using selected available genotypes as parents. Characteristics important to the breeder in the development of peach and nectarine varieties for culture in Florida are chilling requirements which would allow for stone fruit production in regions of mild or warm winters, and production of fruit in a season which would appeal to the consumer. For example, one which would have attractive size, appearance, shape, taste and aroma and which would capture the premium prices for early fruit in a given market. The present invention relates to a new distinct variety of nectarine tree, which is named 'Sunmist'; and, which I developed in such a planned breeding program. In the disclosure to follow comparison is made to 'Sunred' nectarine, an old standard variety, for reliable description and contrast.

ASEXUAL REPRODUCTION OF THE VARIETY

Asexual propagation of this tree has been performed at Gainesville, Fla., by me or under my direction, by budding, where the selection was made and tested.

ORIGIN OF THE VARIETY

This nectarine tree (genotype) was originated by me in the tree fruit breeding plots at the University of Florida, located at Gainesville, Fla. The seed parent was 'Flordaglo' (unpatented), a white flesh peach (which is heterozygous for nectarine) and the pollen parent was 'Mayfire' (unpatented) nectarine. 'Sunmist' nectarine was selected as the eleventh selection in 1988; exhibited white flesh and thus was designated "Fla. 88-11NW". It was propagated asexually as a uniform variety and determined to have unique tree and fruit characteristics making it worthy for commercial production. 'Sunmist' continues to transmit uniformity through three successive standard asexual propagations by budding.

SUMMARY OF THE VARIETY

The new and distinct variety of nectarine tree bears early-ripening, white flesh fruit, and has a low-chilling dormancy requirement. 'Sunmist' blooms 2 to 3 days following 'Sunred' nectarine at Gainsville and is the only nectarine variety with such a low-chilling dormancy requirement. In further characterization, 'Sunmist' is the only nectarine variety with such a low-chilling requirement that bears large, firm early-ripening, white flesh, when grown in subtropical climates, to take maximum advantage of its early bloom and low chilling requirements. 'Sunmist' will be the first quality commerical white flesh nectarine variety in the USA to ripen. When fruit of this tree ripens in drought stress or in hot climates, the fruit skin is subject to the speckling characteristics of nectarines of a high sugar content that are grown in such under such conditions.

The present invention, resulting in the 'Sunmist' nectarine tree, is characterized by fruit of excellent flavor and eating quality from a tree adapted to culture in regions having mild winter conditions. The trees are vigorous, productive and regular bearing. Trees attain in two years a height of three meters and a spread of two meters at Gainsville. Terminal growth of up to a meter is common on mature five year old trees. The first fruit mature in early May at Gainesville or in about 85 days after full bloom. The fruit are uniformly large for an early ripening nectarine. Fruit have a high percentage of red skin color. The variety was developed by hybridizing 'Flordaglo' peach with 'Mayfire' nectarine. The flower anthers are dark red, a characteristic of less than 10 percent of all standard, peach and nectarine varieties.

The tree, flowers and fruit of this tree may vary in slight detail due to variations in soil type, cultural practices, and climatic conditions. The present botanical description is that of the variety grown under the ecological conditions prevailing near Gainesville, Fla.

BRIEF DESCRIPTION OF THE FIGURES OF THE DRAWING

The accompanying figures of the drawing photographically show typical specimens of the fruit and leaves of the new variety in color as nearly true as it is reasonably possibke to make in color illustrations of this type, wherein.

Figure 1:
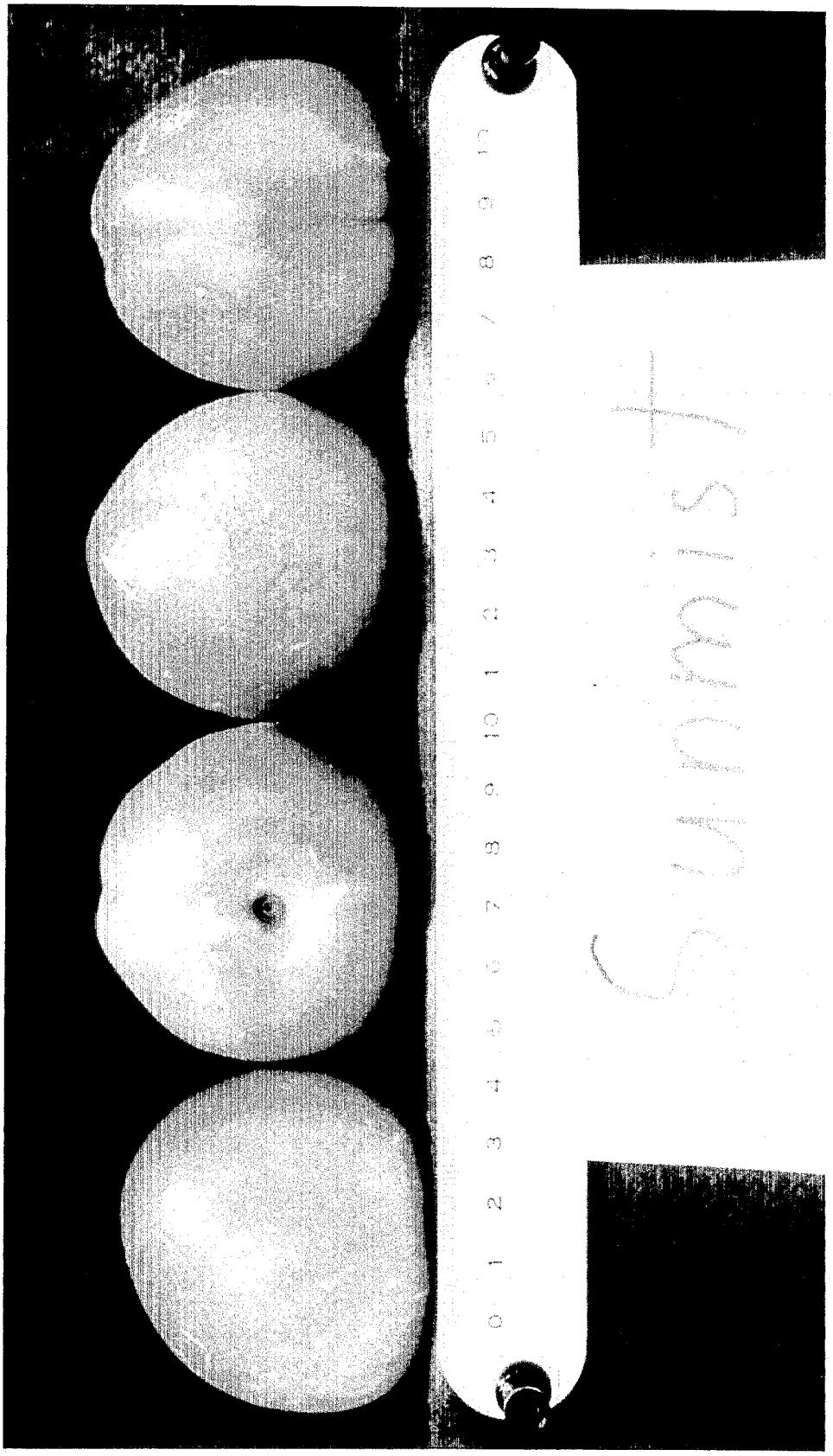
FIG. 1 shows the attractive shape and exterior coloration of four specimens of fruit about a ruler in side view, stem and view, a blossom end view, and side view showing the suture.
Figure 2:
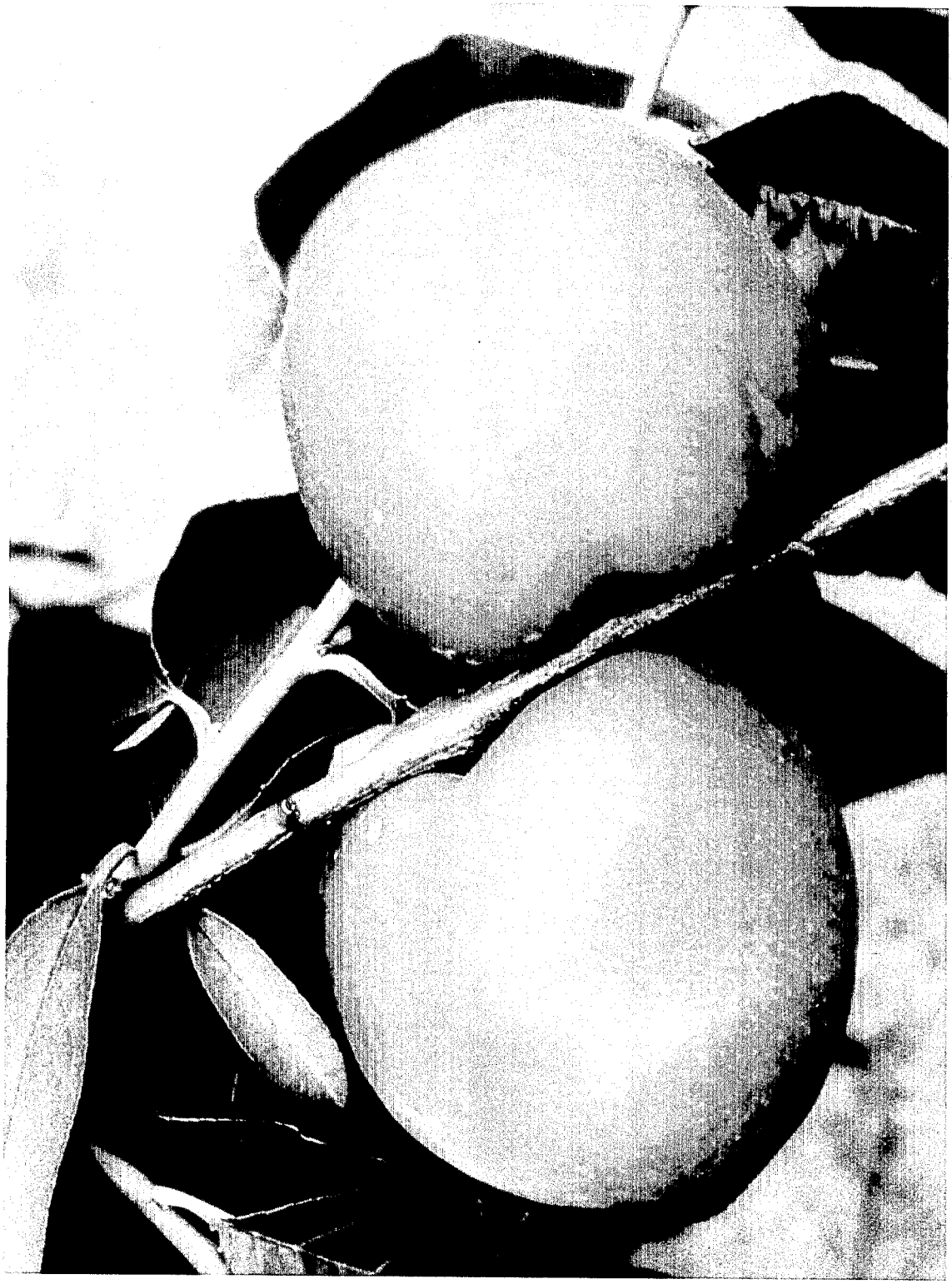
FIG. 2 depicts bark of the new and fruiting wood, internode length, leaves, glands, leaf steams and axillary buds, and two specimens of fruit at the harvest ripe stage; and, FIG. 3 illustrates, in close-up view, the fruit skin blemishing which occurs with the culture of this tree in very warm climates.
Figure 3:
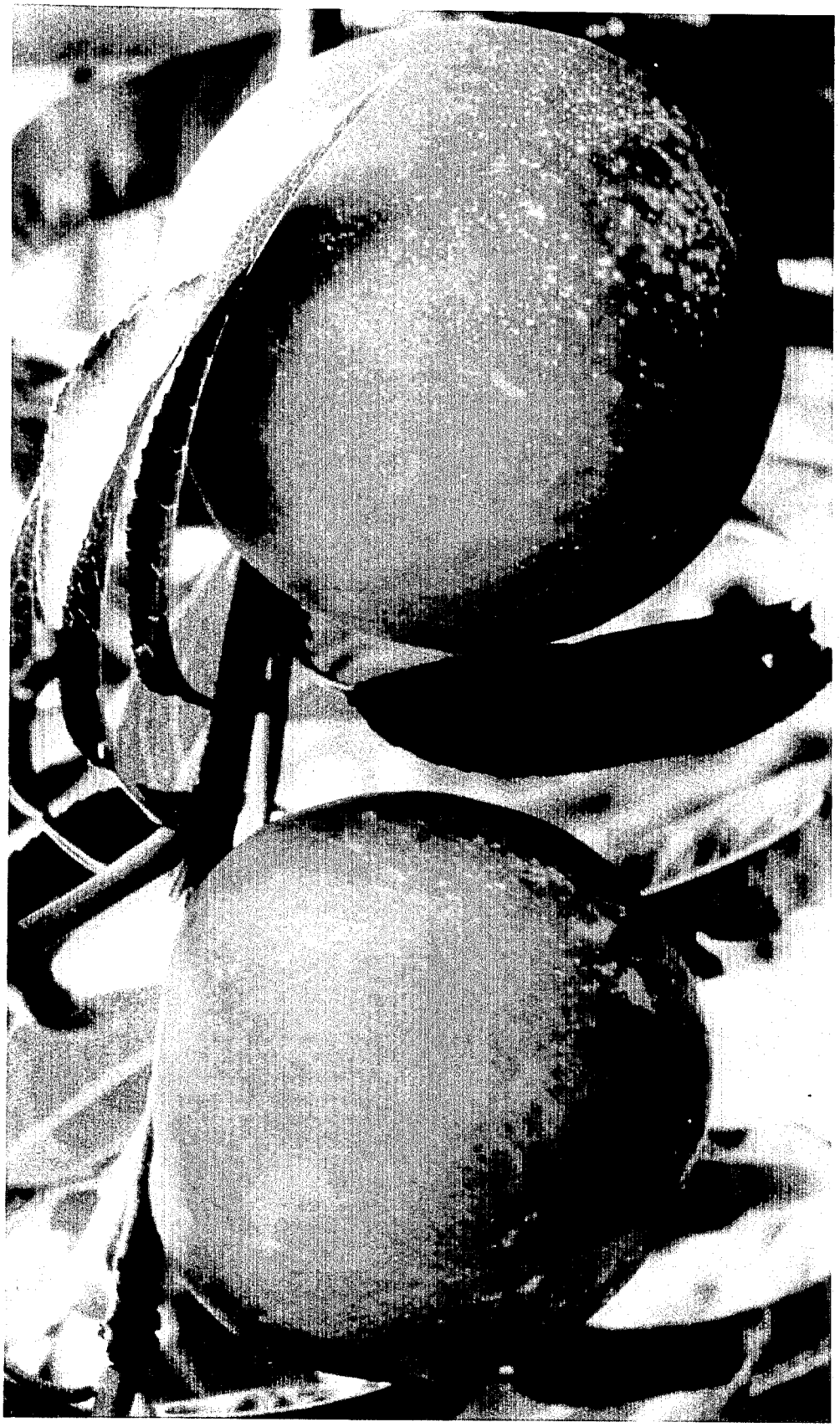

The fruit of the drawing was taken at a maturity stage of firm ripe at the above noted location of culture. Colors described from *A Dictionary of Color*, published by the McGraw Hill Co., Inc., New York, 1930.

DETAILED BOTANICAL DESCRIPTION OF THE VARIETY

In general, the tree of this disclosure is adapted for culture in regions having warmer seasons within temperate and subtropical zones due to its uncommonly low winter chilling requirement of about 300 chill units. Other notable characteristics which help immediately distinguish this tree are its large size, high level of vigor, spreading habit and showy pink flowers. Flowers have terra cotta (red) anthers. Glands are reniform in shape and isolated to the basal portions of the leaves. It is a regular bearer of heavy crops of early maturing fruit which is large for the season and attractively uniform in shape and coloration. The fruit is very symmetrical in shape, has a shallow suture, and is nearly solidly overcolored with ruby to red to result in a very high level of eye appeal. Fruit ripens substantially with that of 'Sunred', but is larger, firmer and of very good eating quality. The tree has been systematically botanically observed to have the following botanical characteristics.

Tree:
- *Size.*—Large.
- *Vigor.*—Vigorous, must be pruned to keep tree height to desired height.
- *Density.*—Medium to dense.
- *Form.*—Upright when pruned to vase shape.
- *Bearer.*—Regular, must be fruit thinned to avoid limb breakage and to obtain larger fruit size.

Trunk:
- *Size.*—Medium.
- *Thickness.*—Medium.
- *Texture.*—Medium smooth.
- *Bark Color.*—Older bark—Gray brown (Plate 14, line 1A), new bark—(Plate 13, line 1A).

Lenticels:
- *Amount.*—Medium.
- *Size.*—Medium.
- *Shape.*—Medium.
- *Color.*—(Plate 13, line 2B).

Branches:
- *Size.*—Normal.
- *Texture.*—Relatively smooth, medium amount of lenticels.
- *Color.*—New wood—Green. Mature wood—Brown.

Leaves:
- *Size.*—Medium.
- *Thickness.*—Regular.
- *Form.* —Lanceolate.
- *Apex.*—Acute.
- *Margin.*—Serrulate.
- *Base.*—Coneate.
- *Surface.*—Glabrous.
- *Color.*—Upper—Polo green (Plate 23, line 9J). Lower—Garland green (Plate22, line I7).
- *Glands.*—Two, small, globose glands on upper petiole and lower leaf blade, except up to six glands on vigorous shoots.
- *Petiole.*—About 1 cm (0.7 to 1.1 cm).
- *Stipules.*—None present.

Flower buds:
- *Abundance-* Moderately high.
- *Size.*—Medium.
- *Length.*—Medium.
- *Shape.*—Plump.
- *Surface.*—Pubescent.

Flowers:
- *Blossom period.*—2 to 3 days after 'Sunred' nectarine.
- *Dates.*—Average about February 8–15 at Gainesville, Fla.
- *Size.*—Large, showy.
- *Color.*—Pink 4T (Plate 1, line A2 to D2), darkening to cameo pink (Plate 50, line 2C to 2G and line 3C to 3G).
- *Anthers.*—Dark red, terra cotta (algonquin), (Plate 4, line 12A to 12D).
- *Pollen.*—Abundant and bright yellow (common to many varieties).
- *Fertility.*—Self-fertile.

Fruit:
- *Maturity when described.*—Firm to first eating ripe, May 1, 1994.
- *Date for first picking.*—Apr. 22, 1994.
- *Size.*—Uniform, medium large (large size for early maturity). Average diameter axially—2¼ inches (57 mm). Average length—2¼ inches (57 mm).

Form:
- *Longitudinal section form.*—Round.
- *Transverse section through diameter.*—Round.
- *Suture.*—Shallow and inconspicuous.
- *Ventral surface.*—Rounded.
- *Base.*—Slightly retuse.

Cavity:
- *Shape.*—Flaring, circular.
- *Depth.*—¼ to ⅜ inch (6 to 9 mm).
- *Breadth.*—⅝ inch (16 mm).
- *Apex.*—Rounded.

Stem:
- *Size.*—Medium.
- *Average length.*—¼ to ⅜ inch (6–9 mm).
- *Average width.*—5/32 inch (3 mm).

Skin:
- *Thickness.*—Medium.
- *Texture.*—Medium.
- *Tenacity.*—Tenacious to flesh.
- *Color.*—Plate 6,(lines 6A through 6L).
- *Tendency to crack.*—None observed.

Flesh:
- *Ripens.*—Evenly.
- *Texture.*—Firm, juicy, crisp, melting when fully ripe.
- *Fibers.*—Very fine, tender, small.
- *Aroma.*—Very high.
- *Eating quality.*—Very good, very sweet, subacid.
- *Juice.*—Abundant.
- *Color.*—White (Plate 10, line A1) with no redness at pit.
- *Browning by oxidation.*—Moderate.

Stone:

*Type.*—Fully ripe—Freestone. Firm ripe—Semi-freestone.

*Size.*—Medium small.

*Average length.*—30 mm.

*Average width.*—23 mm.

*Color.*—Saratoga (Plate 11, line 8J).

*Form.*—Oblong.

*Base.*—Straight.

*Apex.*—Acute.

*Sides.*—Equal.

*Surface.*—Irregulary furrowed toward the ventral edge.

*Ridges.*—Jagged toward the base.

*Pit Wall.*—3/16 to 1/4 inch thick (5–6 mm).

*Tendency to split.*—None observed.

Use: Fresh; dessert.

Resistance to disease: High resistance to bacterial spot incited by *Xanthomonas campestris*.

Keeping quality: Good.

Shipping quality: Degree of firmness at harvest and firmness retained in refrigeration indicates fruit should be highly acceptable for shipping.

I claim:

1. A new and distinct variety of nectarine tree, as illustrated and described, characterized by a low chilling requirement and bearing early-ripening fruit with white flesh and high eating quality, and with aroma typically associated whith white flesh.

* * * * *